(12) United States Patent
Mizutani et al.

(10) Patent No.: US 8,663,185 B2
(45) Date of Patent: Mar. 4, 2014

(54) WEARING ARTICLE

(75) Inventors: Katsumi Mizutani, Kagawa (JP); Haruki Toda, Kagawa (JP); Maiko Suzuki, Kagawa (JP); Yoshikazu Tanaka, Kagawa (JP)

(73) Assignee: Unicharm Corporation, Ehime (JP)

( * ) Notice: Subject to any disclaimer, the term of this patent is extended or adjusted under 35 U.S.C. 154(b) by 456 days.

(21) Appl. No.: 12/865,906

(22) PCT Filed: Nov. 20, 2008

(86) PCT No.: PCT/JP2008/071079
§ 371 (c)(1),
(2), (4) Date: Nov. 4, 2010

(87) PCT Pub. No.: WO2009/098811
PCT Pub. Date: Aug. 13, 2009

(65) Prior Publication Data
US 2011/0046597 A1    Feb. 24, 2011

(30) Foreign Application Priority Data

Feb. 4, 2008  (JP) .................................. 2008-024451

(51) Int. Cl.
*A61F 13/15*    (2006.01)
(52) U.S. Cl.
USPC ........................................ 604/391; 604/385.3
(58) Field of Classification Search
USPC ............. 604/385.24–385.27, 385.3, 391, 389
See application file for complete search history.

(56) References Cited

U.S. PATENT DOCUMENTS

| 5,326,612 | A | 7/1994 | Goulait | |
| 6,572,602 | B2 * | 6/2003 | Furuya et al. | 604/391 |
| 2003/0109844 | A1 * | 6/2003 | Gibbs | 604/389 |

(Continued)

FOREIGN PATENT DOCUMENTS

| JP | 1-168510 | 11/1989 |
| JP | 6-507800 | 9/1994 |

(Continued)

OTHER PUBLICATIONS

International Search Report from corresponding PCT/JP2008/071079 dated Feb. 24, 2009, 6 pages.

*Primary Examiner* — Lynne Anderson
(74) *Attorney, Agent, or Firm* — Brinks Gilson & Lione

(57) ABSTRACT

The present invention aims to provide a wearing article improved so that various types of nonwoven fabrics can be effectively used for target nonwoven fabric without anxiety that the target nonwoven fabric once engaged with hook elements might be readily torn. As an outer sheet 8 defining a garment-facing side of a chassis 2, a commonly-used nonwoven fabric is used and this nonwoven fabric is oriented in a longitudinal direction Y. Rear waist region's side edges 14 of the chassis 2 are provided with flaps 16 attached thereto. Each of the flaps 16 has a joint region 19 along which the flap 16 is joined to the chassis 2 and first and second hook elements 21, 22. Between the joint region 19 and the first and second hook elements 21, 22 as viewed in the transverse direction X, a contractible region 23 adapted to be contractible in the transverse direction X. The contractible region 23 is provided with a plurality of flap's elastic members 24. The joint region 19 provided with none of the flap's elastic members 24 define a non-contractible region. The first and second hook elements 21, 22 of the flap 16 may be put in engagement with the outer sheet 8 to connect the front and rear waist regions 4, 5 to each other in a circumferential direction.

21 Claims, 6 Drawing Sheets

(56) References Cited

U.S. PATENT DOCUMENTS

| | | |
|---|---|---|
| 2005/0027279 A1 | 2/2005 | Minato et al. |
| 2005/0222551 A1 | 10/2005 | Otsubo et al. |
| 2006/0241560 A1* | 10/2006 | Chang et al. ............. 604/385.31 |
| 2007/0005037 A1 | 1/2007 | Mansfield et al. |
| 2007/0066950 A1* | 3/2007 | Nelson .......................... 604/389 |
| 2007/0142808 A1* | 6/2007 | Wada et al. ................ 604/385.3 |

FOREIGN PATENT DOCUMENTS

| | | |
|---|---|---|
| JP | 2001-087309 | 4/2001 |
| JP | 2003-180748 | 7/2003 |
| JP | 2005-46225 | 2/2005 |
| JP | 2005-245555 | 9/2005 |
| JP | 2005-287821 | 10/2005 |
| WO | WO 2007/002929 A2 | 1/2007 |

* cited by examiner

FIG.2
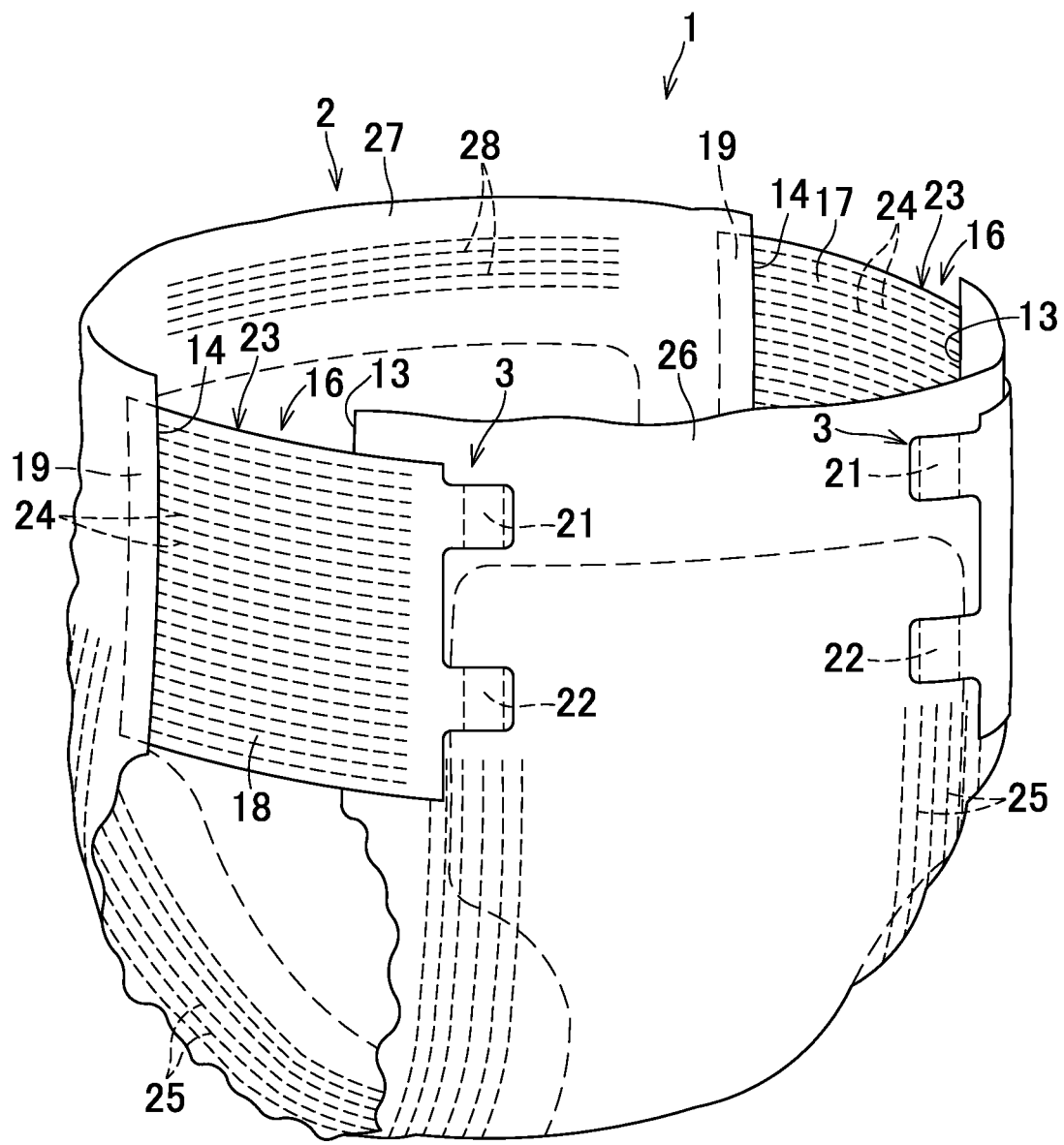
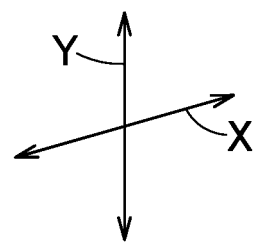

FIG.3
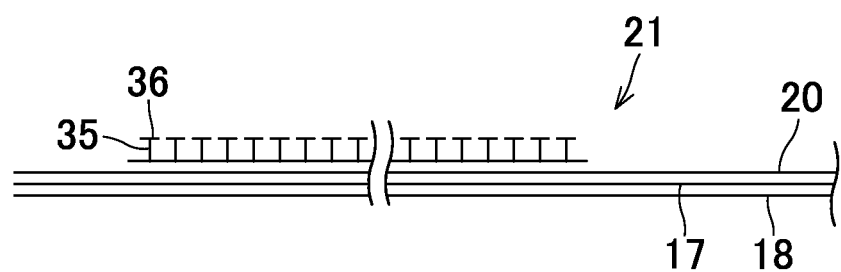
FIG.4
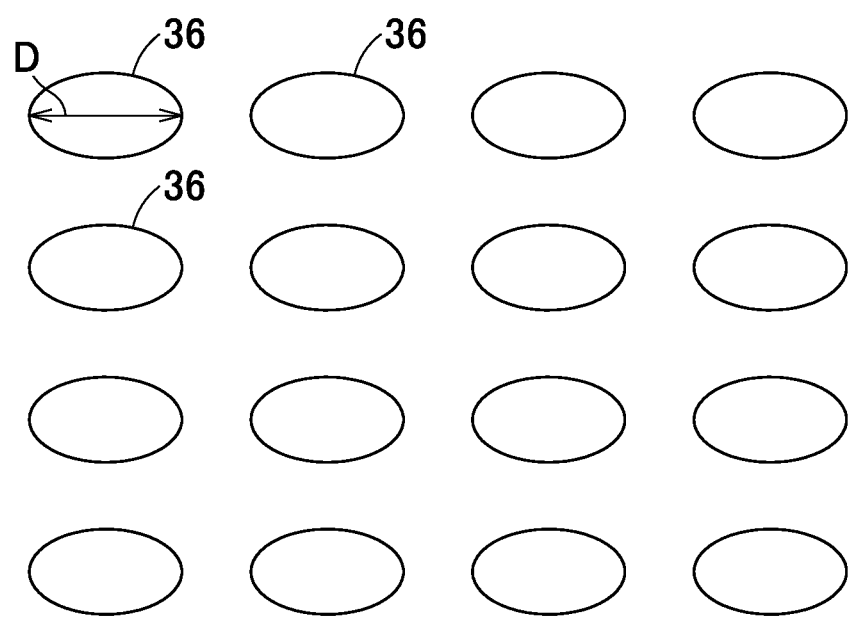
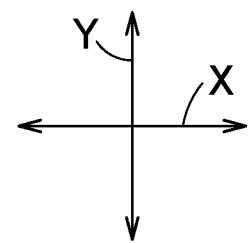

WEARING ARTICLE

RELATED APPLICATION

This application is a 35 U.S.C. §371 national phase filing of International Patent Application No. PCT/JP2008/071079, filed Nov. 20, 2008, through which and to which priority is claimed under 35 U.S.C. §119 to Japanese Patent Application No. 2008-024451, filed Feb. 4, 2008.

TECHNICAL FIELD

The present invention relates to wearing articles and more particularly to wearing articles such as disposable diapers, toilet-training pants or incontinent briefs.

RELATED ART

Disposable diapers adapted to be handled for actual use so that front and rear waist regions maybe joined together to form so-called pant-type diaper is known, for example, from JP 2003-180748 A (PATENT DOCUMENT 1). According to the disclosure of this PATENT DOCUMENT 1, the diaper comprises front and rear waist regions and a chassis has a skin-facing side and a garment-facing side. The chassis has an inner sheet defining the skin-facing side and an outer sheet defining the garment-facing side wherein the outer sheet is formed of an air-through fibrous nonwoven fabric and the inner sheet of the rear waist region is provided with hook elements. The hook elements maybe put in engagement with the outer sheet of the front waist region to join the front and rear waist region together and thereby the diaper is pant-shaped.

By using a fibrous nonwoven fabric as a target with which the hook elements are put in engagement, it is possible to eliminate use of loop elements operatively associated with the hook elements and a manufacturing cost can be correspondingly saved. From another viewpoint, by eliminating use of the loop elements, sound generated at the moment of disengaging the hook elements from the loop elements. More specifically, when the engagement of the hook elements with the loop elements is used, rather offensive sound is inevitably generated when the hook elements are disengaged from the loop elements. For example, in a hospital room shared by two or more patients, diaper exchange of any one patient in the middle of the night may often make the other patient sensible and such problem is solved by the diaper disclosed in PATENT DOCUMENT 1.

PATENT DOCUMENT 1: JP 2003-180748 A

DISCLOSURE OF THE INVENTION

Problem to be Solved by the Invention

However, when the method of engaging the hook elements with the target fibrous nonwoven fabric is employed, there is a problem that the engaging strength is lower than the case in which the hook elements are put in engagement with the loop elements so that the hook elements might be disengaged from the target fibrous nonwoven fabric when the diaper is put on the wearer's body.

According to the disclosure of PATENT DOCUMENT 1, an air-through nonwoven fabric characterized by the relatively short fiber length is used as the target fibrous nonwoven fabric. However, the air-through nonwoven fabric is often torn as the wearer sits down after the hook elements have been put in engagement with the air-through nonwoven fabric. Specifically, such movement of the wearer stretches the peripheral edges of the respective leg-openings and consequently the front and rear waist regions also are pulled in the transverse direction. Thereupon, excessively high tensile force is generated in a shearing direction between the air-through nonwoven fabric and the hook elements which have been once engaged, and eventually the air-through nonwoven fabric may be torn. This is for the reason that the fiber length of the air-through nonwoven fabric is short and the number of interfacing points is insufficient.

In addition, the target fibrous nonwoven fabric is limited to the air-through nonwoven fabric in this diaper of prior art and therefore it is impossible to select the type of the nonwoven fabric depending on intended purpose.

In view of the problem as has been described above, it is a principal object of the present invention to provide a wearing article improved so that various types of nonwoven fabrics can be effectively used for target nonwoven fabric without anxiety that the target nonwoven fabric once engaged with hook elements might be readily torn.

Measure to Solve the Problem

The object set forth above is achieved, according to the present invention, by an improvement in a wearing article comprising a chassis having a longitudinal direction and a transverse direction, a skin-facing side and a garment-facing side and a front waist region, a rear waist region and a crotch region extending between these front and rear waist regions and having fastening means serving to connect respective opposite side edges of the front and rear waist regions in a detachable manner and thereby to connect the front and rear waist regions to each other in a circumferential direction.

The improvement according to the present invention is characterized in that: the fastening means comprise hook elements provided on one of the front and rear waist regions and a target fibrous nonwoven fabric provided on the other of the front and rear waist regions and adapted to be detachably engaged with the hook elements; and contractible regions adapted to be contractible in the transverse direction are provided inboard of said hook elements as viewed in said transverse direction.

According to one preferred embodiment of the present invention, the chassis comprises an inner sheet defining the skin-facing side and an outer sheet defining the garment-facing side; and the outer sheet is formed of the target fibrous nonwoven fabric.

According to another preferred embodiment of the present invention, non-contractible regions having no elasticity are formed contiguously to respective the contractible regions.

According to still another preferred embodiment of the present invention, the target fibrous nonwoven fabric comprising component fibers oriented in the longitudinal direction.

According to yet another preferred embodiment of the present invention, the chassis includes leg-surrounding elastic members attached under tension along the side edges to extend in the longitudinal direction and the contractible regions cooperate with the leg-surrounding members as the diaper is put on the wearer's body to form annular peripheral edges of the respective leg-openings.

According to further another preferred embodiment of the present invention, the contractible regions include a plurality of elastic members or elastic nonwoven fabric ribbons, and the elastic members or the elastic nonwoven fabric ribbons are attached under tension to the contractible regions to be spaced one from another in the longitudinal direction and to extend in the transverse direction.

Effect of the Invention

The fastening means comprise the hook elements provided on one of the front and rear waist regions and the target fibrous nonwoven fabric provided on the other of the front and rear waist regions and adapted to be detachably engaged with the hook elements to connect the front and rear waist regions with each other. With such arrangement, the sound generated in the course of putting or exchanging the diaper on or from the wearer's body can be minimized. Inboard of the hook elements as viewed in the transverse direction, there are provided the contractible regions adapted to be elastically contractible in the transverse direction so that the shear force generated from the tensile stress thereof may reinforce the engagement between the hook elements and the target nonwoven fabric. With the engagement reinforced in this manner, the target nonwoven fabric is not limited to a particular type of nonwoven fabric but various types of nonwoven fabric may be selectively employed as the target nonwoven fabric.

The chassis comprises the inner sheet defining the skin-facing side and the outer sheet defining the garment-facing side. The outer sheet is formed of the target fibrous nonwoven fabric and the article can be produced without any loop elements. Therefore, the manufacturing cost can be correspondingly reduced.

The non-contractible regions having none of elastic members are formed inboard of the respective contractible regions as viewed in the transverse direction. When the diaper is pulled in opposite directions with the hook elements or the regions in vicinities thereof gripped by the fingers, the above-described arrangement allows the pull force to be transmitted to the chassis as a whole by the intermediary of the non-contractible regions and therefore the position of the wearing article on the wearer's body can be adjusted with the hook elements or the regions in vicinities thereof gripped by the fingers.

The target fibrous nonwoven fabric comprises component fibers oriented in the longitudinal direction. The hook elements deeply bite into the target nonwoven fabric as the contractile force of the contractible regions acting to pull the hook elements which have already been put in engagement with the target nonwoven fabric in the transverse direction is exerted to the hook elements. In this way, these hook elements and the target nonwoven fabric can be further firmly engaged together.

The chassis includes the leg-surrounding elastic members attached under tension along the side edges to extend in the longitudinal direction and the contractible regions cooperate with the leg-surrounding members as the diaper is put on the wearer's body to form the annular peripheral edges of the respective leg-openings. In other words, the leg-openings' peripheral edges can be defined by the leg-surrounding elastic members and the contractible regions so that the peripheral edges of the respective leg-openings may smoothly follow movement of the wearer's body and thereby alleviate tensile force in the shearing direction exerted on the fastening means.

The contractible regions include a plurality of elastic members or elastic nonwoven fabric ribbons, attached under tension to the contractible regions to be spaced one from another in the longitudinal direction and to extend in the transverse direction. With such arrangement, the portions defined between each pair of the adjacent elastic members or the elastic nonwoven fabric ribbons assure the air-permeability and the flexibility. It should be noted that use of the elastic members is more preferable than use of the elastic nonwoven fabric ribbons from the viewpoint of durability and manufacturing cost.

BRIEF DESCRIPTION OF THE DRAWINGS

FIG. 2 is a perspective view showing the diaper as put on the wearer's body.

FIG. 3 is a sectional view taken along the line III-III in FIG. 1.

FIG. 4 is a diagram illustrating hook elements in an enlarged scale.

Figure 1:
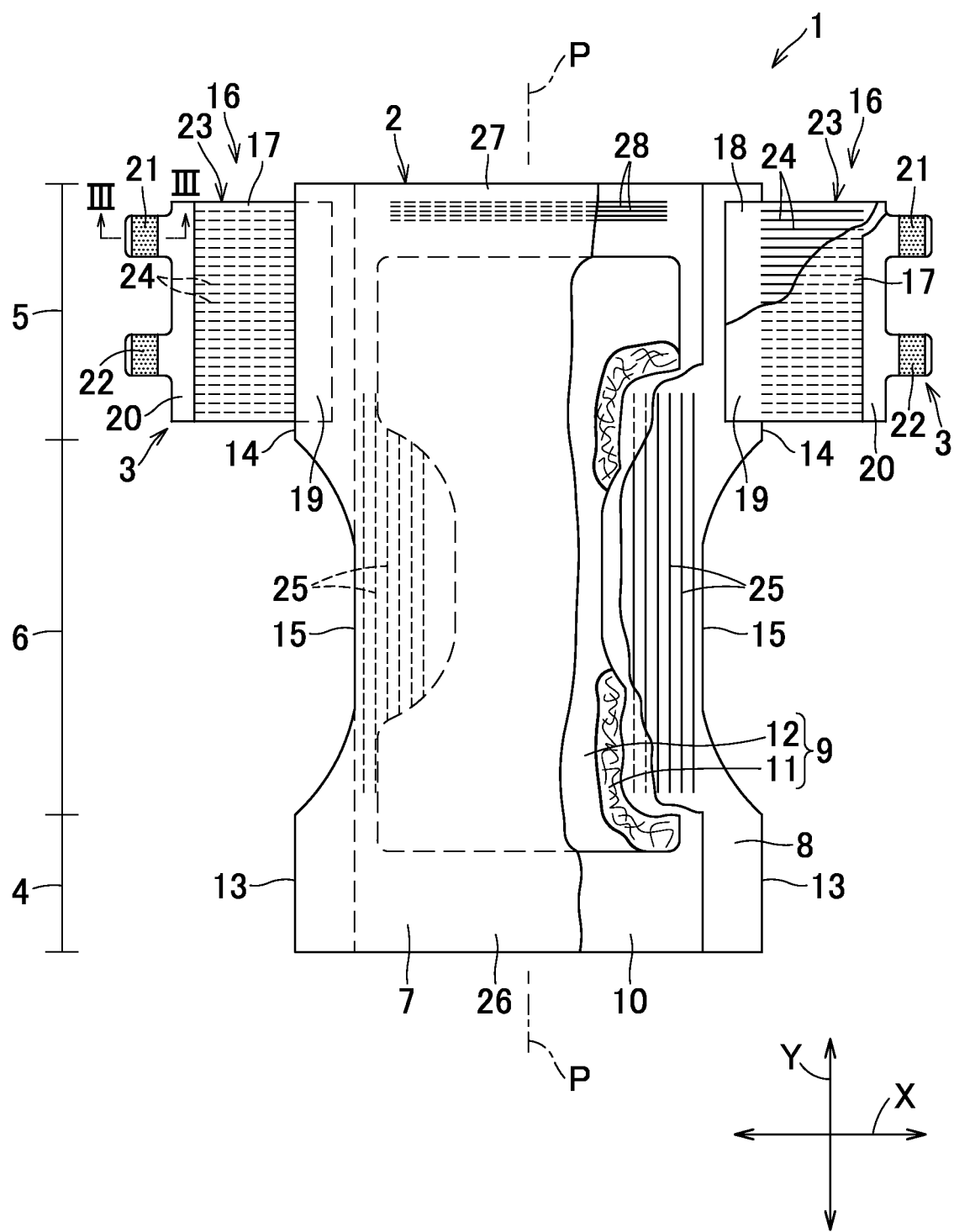
FIG. 1 is a plan view showing the diaper according to a first embodiment of the present invention as kept in flatly developed.

| IDENTIFICATION OF REFERENCE NUMERALS USED IN THE DRAWINGS | |
|---|---|
| 1 | diaper |
| 2 | chassis |
| 3 | fastening means |
| 4 | front waist region |
| 5 | rear waist region |
| 6 | crotch region |
| 7 | inner sheet |
| 8 | outer sheet |
| 13 | front waist region's side edges |
| 14 | rear waist region's side edges |
| 19 | joint regions |
| 21 | first hook elements |
| 22 | second hook elements |
| 23 | contractible regions |
| 24 | flaps' elastic members |

DETAILED DESCRIPTION OF THE PREFERRED EMBODIMENTS

First Embodiment

FIGS. 1 through 4 illustrate the first embodiment of the present invention. FIG. 1 is a plan view showing so-called open-type disposable diaper as partially cutaway for convenience of illustration. The diaper 1 comprises a liquid-absorbent chassis 2 and fastening means 3 attached to the chassis 2. The chassis 2 has front and rear waist regions 4, 5 and a crotch region 6 extending between these front and rear waist regions 4, 5. This chassis 2 comprises an inner sheet 7 defining the skin-facing side, an outer sheet 8 defining the garment-facing side, a liquid-absorbent structure 9 sandwiched between these inner and outer sheets 9 and a leak-barrier sheet 10 sandwiched between the liquid-absorbent structure 9 and the outer sheet 8.

The inner sheet 7 may be formed, for example, by an air-permeable nonwoven fabric. The liquid-absorbent structure 9 comprises a core 11 formed, for example, by mixture of fluff pulp and super-absorptive polymer particles and tissue paper 12 wrapping the core 11. The leak-barrier sheet 10 has a size sufficiently large to cover at least the liquid-absorbent structure 9 and adapted to prevent leakage of bodily fluids from the liquid-absorbent structure 9 toward the wearer's garment. The leak-barrier sheet 10 may be formed, for example, of a liquid-impervious plastic film. The outer sheet 8 may be formed of a commonly used nonwoven fabric such as an air through nonwoven fabric, a spun bonded nonwoven fabric or a point bonded nonwoven fabric. Preferably, the outer sheet 8 is formed of a spun bonded nonwoven fabric or a point bonded nonwoven fabric. This is for the reason that, compared to the spun bonded nonwoven fabric and the point bonded nonwoven fabric, the air through nonwoven fabric has problematic features, specifically, bulkiness and short fiber length resulting in insufficient number of interlacing points, to be used as stock material for the outer sheet 8. Particularly the latter feature may cause the outer sheet 8 to be readily broken as the outer sheet 8 is engaged with the hook elements. While the stock material for the outer sheet 8 may be selected from several types of nonwoven fabric depending on the characteristics required, the fiber orientation in the longitudinal direction Y is essential condition in each case.

The chassis 2 has a concaved shape curved inwardly defined by the inner and outer sheets 7, 8 and is symmetric about a longitudinal center line P-P bisecting a dimension of the chassis 2 in a transverse direction X. The chassis 2 has front waist region's side edges 13, rear waist region's side edges 14 and crotch region's side edges 15 respectively opposed to each other in the transverse direction X and extending in the longitudinal direction Y in the front waist region 4, the rear waist region 5 and the crotch region 6. The crotch region's side edges 15 are concaved cut out with respect to the front and rear waist regions' side edges 13, 14 to define the inwardly-curved shape.

The rear waist region's side edges 14 are respectively provided with flaps 16 joined thereto. Each of the flaps 16 comprises a pair of flap sheets 17, 18 which are substantially same in shape as well as in size. As stock material for these flap sheets 17, 18, for example, a liquid-impervious nonwoven fabric may be used. These sheets 17, 18 constituting the flap 16 are partially joined to the inner sheet 7 and the outer sheet 8, respectively, along the rear waist region's side edge 14 by heat sealing or adhesion to define a joint region 19. The respective joint regions 19 are formed to extend in the longitudinal direction Y along the rear waist region's side edges 14.

Along an outer lateral region of the flap 16 opposite to the joint region 19 as viewed in the transverse direction X, a reinforcing sheet 20 is joined to the flap sheet 17 by heat sealing or adhesion. The reinforcing sheet 20 is provided with first and second hook elements 21, 22 spaced from each other in the longitudinal direction Y.

Between the joint region 19 of the flap 16 and the reinforcing sheet 20, a contractible region 23 adapted be elastically contractible in the transverse direction X. The contractible region 23 is formed by attaching a plurality of flap's elastic members 24 extending in the transverse direction X under tension to the flap 16. More specifically, these elastic members 24 are attached between the flap sheets 17, 18 to be spaced one from another generally at regular intervals in the longitudinal direction Y and attached to at least one of the flap sheets 17, 18 by heat sealing or adhesion. The flap's elastic members 24 are not attached to the joint region 19 and, in the other words, inboard of the contractible region 23 as viewed in the transverse direction X, a non-contractible region is defined here at least by the joint region 19. It should be appreciated here that the non-contractible region can be defined not only by the joint region 19 but also, for example, by the section of the flap 16 lying outboard of the joint region 19 as viewed in the transverse direction X and having none of the flap's elastic members 24 attached thereto or the section of the chassis 2 lying inboard of the joint region 19 as viewed in the transverse direction X and having none of elastic members.

Inboard of the crotch region's side edges 15 of the chassis 2, a plurality of leg-surrounding elastic members 25 extending in the longitudinal direction Y are sandwiched between the outer sheet 8 and the leak barrier sheet 10. Specifically, these leg-surrounding elastic members 25 are spaced one from another in the transverse direction X and attached under tension thereto. It is essential for these leg-surrounding elastic members 25 to extend in the longitudinal direction Y at least across the crotch region 6. These leg-surrounding elastic members 25 allow the crotch region 6 to fit around the wearer's legs and thereby prevent leakage of bodily fluids such as urine beyond peripheral edges of respective leg-openings.

The contractible regions 23 defined by flaps' elastic members 24 are arranged to lie outboard of the leg-surrounding elastic members 25 as viewed in the transverse direction X.

The chassis 2 has front and rear ends 26, 27 defined by the front and rear waist regions 4, 5, respectively, to be opposed to each other in the longitudinal direction Y and to extend in the transverse direction X. Along the rear end 27, the chassis 2 is provided with a plurality of waist-surrounding elastic members 28 attached under tension thereto. These waist-surrounding elastic members 28 are spaced one from another in the longitudinal direction Y and sandwiched and joined between the inner sheet 7 and the leak-barrier sheet 10 by heat sealing or adhesion. The waist-surrounding elastic members 28 allow the diaper 1 to fit around the wearer's waist and thereby prevent leakage of bodily fluids such as urine beyond the waist edge.

The waist-surrounding elastic members 28 are attached to the rear end 27 generally in a middle region as viewed in the transverse direction X and respective opposite ends of these elastic members as viewed in the transverse direction X do not reach the respective joint regions 19. Alternatively, sections defined inboard of the respective joint regions 19 as viewed in the transverse direction X and not provided with the waist-surrounding elastic members 28 may cooperate with the respective joint regions 19 to form the non-contractible regions.

FIG. 2 is a diagram illustrating the diaper 1 put on the wearer's body. To wear the diaper 1, the first and second hook elements 21, 22 of the respective flaps 16 are put in engagement with the outer sheet 18 and thereby the front and rear waist regions 4, 5 are connected to each other in circumferential direction. More specifically, a fibrous nonwoven fabric forming the outer sheet 8 is used as a target for the first and second hook elements 21, 22 and these first and second hook elements 21, 22 cooperate with the outer sheet 8 to form fastening means 3.

When the first and second hook elements 21, 22 are put in engagement with the outer sheet 8, the first and second hook elements 21, 22 or the respective reinforcing sheets 20 of the flaps 16 may be pulled toward the longitudinal center line P-P. In response to this, the flaps' elastic members 24 contiguous to the first and second hook elements 21, 22 or the respective reinforcing sheets 20 of the flaps 16 are stretched. After the first and second hook elements 21, 22 have been put in engagement with the outer sheet 8, the flaps' elastic members 24 contract in the transverse direction X. Upon contraction of the flaps' elastic members 24, the first and second hook elements 21, 22 are pulled toward the side of the flaps' elastic members 24 to generate shear force between the first and second hook elements 21, 22 and the outer sheet 8. The outer sheet 8 is fiber oriented in the longitudinal direction Y and such fiber orientation of the outer sheet 8 ensures that the first and second hook elements 21, 22 firmly bite into the fibers of the outer sheet 8 and are caught by the fibers. In this way, it is possible to improve an engaging strength between these elements 21, 22 and the outer sheet 8 so that the first and second hook elements 21, 22 are not easily disengaged from the outer sheet 8 in the course of putting the diaper 1 on the wearer's body.

While the engaging strength between the first and second hook elements 21, 22 and the outer sheet 8 depends on the tensile stress of the flaps' elastic members 24 defining the respective contractible regions 23, the tensile stress of the respective contractible regions 23 preferably set to be in a range of 0.2 N to 5.0 N. The tensile stress less than 0.2 N will be scarcely able to improve the engaging strength between the first and second hook elements 21, 22 and the outer sheet 8 and, in consequence, the these hook elements 21, 22 will be readily disengaged from the outer sheet 8 in the course of putting the diaper 1 on the wearer's body. On the other hand, the tensile stress higher than 5.0 N will excessively increase tightening force exerted on the wearer's waist. The excessively high tightening force may eventually cause skin trouble and cause the wearer to experience unacceptable tight feeling.

TABLE 1 shows relationship of shear force versus engaging strength measured between the first and second hook elements 21, 22 and the outer sheet 8. As samples of nonwoven fabrics, two types of spun bonded nonwoven fabrics A and B were used. Measurement was carried out 30 times for each of these two samples A and B and average thereof was calculated. It should be appreciated that the samples A and B were different from each other with respect to the basis weight and the engaging behavior with the hook elements.

The engaging strength was measured by a method comprising steps of: cutting the hook element in each sample dimensioned to be 100 mm in length☐30 mm in width and fibrous nonwoven fabric in each sample dimensioned to be 150 mm in length☐50 mm in width; placing the sample of fibrous nonwoven fabric on a test bench and then placing the sample of hook element on this fibrous nonwoven fabric; reciprocating once a roller of 700 g on the hook element sample to put the hook element sample in engagement with the fibrous nonwoven fabric sample; exerting shear force of 100 g, 300 g or 500 g on the fibrous nonwoven fabric sample and the hook element sample for 10 seconds; trying to peel the hook element sample from the fibrous nonwoven fabric sample at an angle of 135☐ with respect to the test bench at a rate of 300 mm/min; and obtaining an engaging strength (N) between the hook element sample and the fibrous nonwoven fabric sample on the basis of a resistance to this peeling operation.

[Table 1]

TABLE 1

| Measurement Nos. | Shear Force | | | |
|---|---|---|---|---|
| | Control (0 g) | 100 g | 300 g | 500 g |
| <Sample nonwoven fabric A> | | | | |
| 1 | 0.13 | 0.04 | 0.10 | 0.04 |
| 2 | 0.02 | 0.04 | 0.12 | 0.06 |
| 3 | 0.05 | 0.07 | 0.03 | 0.05 |
| 4 | 0.04 | 0.04 | 0.04 | 0.03 |
| 5 | 0.02 | 0.01 | 0.10 | 0.06 |
| 6 | 0.01 | 0.05 | 0.10 | 0.04 |
| 7 | 0.15 | 0.09 | 0.09 | 0.02 |
| 8 | 0.04 | 0.07 | 0.07 | 0.01 |
| 9 | 0.05 | 0.05 | 0.33 | 0.02 |

TABLE 1-continued

| Measurement Nos. | Shear Force | | | |
|---|---|---|---|---|
| | Control (0 g) | 100 g | 300 g | 500 g |
| 10 | 0.04 | 0.11 | 0.10 | 0.06 |
| 11 | 0.03 | 0.13 | 0.16 | 0.11 |
| 12 | 0.23 | 0.07 | 0.03 | 0.10 |
| 13 | 0.06 | 0.10 | 0.06 | 0.07 |
| 14 | 0.07 | 0.13 | 0.05 | 0.10 |
| 15 | 0.09 | 0.16 | 0.09 | 0.07 |
| 16 | 0.05 | 0.11 | 0.07 | 0.06 |
| 17 | 0.14 | 0.04 | 0.09 | 0.07 |
| 18 | 0.01 | 0.07 | 0.05 | 0.13 |
| 19 | 0.03 | 0.06 | 0.05 | 0.08 |
| 20 | 0.03 | 0.05 | 0.07 | 0.11 |
| 21 | 0.04 | 0.05 | 0.11 | 0.09 |
| 22 | 0.02 | 0.08 | 0.04 | 0.11 |
| 23 | 0.04 | 0.14 | 0.13 | 0.04 |
| 24 | 0.04 | 0.05 | 0.05 | 0.05 |
| 25 | 0.02 | 0.05 | 0.06 | 0.12 |
| 26 | 0.02 | 0.10 | 0.10 | 0.07 |
| 27 | 0.07 | 0.10 | 0.08 | 0.15 |
| 28 | 0.06 | 0.10 | 0.06 | 0.07 |
| 29 | 0.07 | 0.21 | 0.09 | 0.03 |
| 30 | 0.16 | 0.03 | 0.08 | 0.13 |
| Average | 0.06 | 0.08 | 0.09 | 0.07 |
| <Sample nonwoven fabric B> | | | | |
| 1 | 0.22 | 0.20 | 0.32 | 0.17 |
| 2 | 0.14 | 0.11 | 0.30 | 0.35 |
| 3 | 0.21 | 0.19 | 0.45 | 0.29 |
| 4 | 0.28 | 0.17 | 0.25 | 0.25 |
| 5 | 0.11 | 0.25 | 0.35 | 0.35 |
| 6 | 0.11 | 0.26 | 0.16 | 0.45 |
| 7 | 0.11 | 0.12 | 0.29 | 0.35 |
| 8 | 0.12 | 0.21 | 0.18 | 0.28 |
| 9 | 0.12 | 0.33 | 0.35 | 0.47 |
| 10 | 0.25 | 0.17 | 0.40 | 0.30 |
| 11 | 0.15 | 0.21 | 0.25 | 0.26 |
| 12 | 0.14 | 0.14 | 0.23 | 0.31 |
| 13 | 0.13 | 0.18 | 0.27 | 0.19 |
| 14 | 0.33 | 0.17 | 0.21 | 0.25 |
| 15 | 0.29 | 0.15 | 0.16 | 0.29 |
| 16 | 0.14 | 0.18 | 0.13 | 0.16 |
| 17 | 0.18 | 0.07 | 0.36 | 0.19 |
| 18 | 0.13 | 0.23 | 0.12 | 0.16 |
| 19 | 0.31 | 0.13 | 0.14 | 0.19 |
| 20 | 0.19 | 0.15 | 0.16 | 0.35 |
| 21 | 0.21 | 0.20 | 0.08 | 0.25 |
| 22 | 0.25 | 0.17 | 0.11 | 0.22 |
| 23 | 0.14 | 0.34 | 0.15 | 0.11 |
| 24 | 0.20 | 0.17 | 0.20 | 0.28 |
| 25 | 0.24 | 0.28 | 0.13 | 0.24 |
| 26 | 0.24 | 0.32 | 0.25 | 0.28 |
| 27 | 0.16 | 0.27 | 0.22 | 0.13 |
| 28 | 0.17 | 0.31 | 0.07 | 0.29 |
| 29 | 0.18 | 0.20 | 0.31 | 0.12 |
| 30 | 0.11 | 0.39 | 0.16 | 0.29 |
| Average | 0.19 | 0.21 | 0.23 | 0.26 |

As indicated in TABLE 1, as control, the measurement was carried out also with respect to the case in which the shear force is 0 g, in other words, no shear force is exerted on the test pieces. Result of measurement demonstrated that, both in the case of the sample nonwoven fabric A and in the case of the sample nonwoven fabric B, the engaging strength becomes noticeably higher when appropriate level of shear force is exerted thereon than when no shear force is exerted thereon.

In two or more samples, the engaging strength was 0.02 N or less under shear force of 0 g. In addition, it was also verified by way of experiment that the hook elements are disengaged from the fibrous nonwoven fabric when the engaging strength is 0.02 N or less. In view of these facts, the shear force is preferably set to at least 20 g or higher and more preferably set to a range of 100 g to 500 g.

FIG. 3 is a scale-enlarged sectional view taken along the line III-III in FIG. 1 and FIG. 4 is a partially scale-enlarged plan view of the first hook elements 21. While the first hook elements 21 will be described hereunder, it should be appreciated that the second hook elements 22 are similar to the first hook elements 21 in arrangement as well as in configuration. As will be apparent from FIG. 3, the individual hook element 21 comprises a shank 35 extending orthogonally to the reinforcing sheet 20 and a claw 36 extending orthogonally to the shank 35. Referring to FIG. 4, the claw 36 has a generally elliptical planar shape of which a major axis D thereof extends in parallel to the transverse direction X. In other words, the first hook elements 21 as a whole are arranged to be oriented in the transverse direction X and correspondingly the claws 6 of the individual first hook elements 21 are relatively long in the transverse direction X. By orienting the respective claws 36 in respective arrays of the first hook elements 21 to be relatively long in the transverse direction X, the respective claws 36 can be smoothly put in engagement with the fibers of the outer sheet 8 oriented in the longitudinal direction Y and the strength of such engagement can be improved. The strength of engagement between the hook elements and the fibrous non-woven fabric depends on particular arrangements of the claws 6 and the result of measurement thereof is shown by TABLE 2. Measurement of the strength of engagement between the hook elements and the fibrous nonwoven fabric was carried out in the same manner in the case of TABLE 1 under the shear force of 300 g.

[Table 2]

TABLE 2

|  | Sample 1 | Sample 2 |
|---|---|---|
| Engaging strength (N) | 0.09 | 0.02 |

In TABLE 2, Sample 1 is of the hook elements arranged so that each of the claws 36 has its major axis D extending in parallel to the transverse direction X in accordance with the embodiment of the present invention and Sample 2 is of the hook elements arranged so that each of the claws has its major axis D extending in parallel to the longitudinal direction Y. In the case of Sample 1 having the claws 36 arranged to be relatively long in the transverse direction X, its strength of engagement with the fibrous nonwoven fabric defining the sample of the outer sheet 8 was 0.09 N and, in the case of Sample 2 having the claws arranged to be relatively long in the longitudinal direction Y, its strength of engagement with the sample of the outer sheet 8 was 0.02 N. In other words, the claws 36 arranged to be relatively long in the transverse direction X assured the strength of engagement with the outer sheet 8 approximately 4.5 times higher than the strength of engagement obtained by the claws 36 arranged to be relatively long in the longitudinal direction. This seems to be for the reason that the claws 36 arranged to be relatively long in the transverse direction X can bite more deeply into the fibrous nonwoven fabric oriented in the longitudinal direction Y than the claws 36 arranged to be relatively long in the longitudinal direction Y.

With the unique arrangement according to the present embodiment as has been described above, component fibers of a fibrous nonwoven fabric serving as the target may be oriented in the longitudinal direction Y to strengthen the engagement of the hook elements with the target fibrous nonwoven fabric and, in addition, the claws each having the elliptical planar shape may be arrayed to be relatively long in the transverse direction X to assure further strengthened engagement. Furthermore, the contractible region 23 adapted to be contractible in the transverse direction X and formed inboard of the hook elements as viewed in the transverse direction X serves to assure reliable engagement of the hook elements with the target fibrous nonwoven fabric. As the hook elements, mechanical fasteners made of polyolefin-based resin are preferably used. While the claws 36 each having a generally elliptical shape are used in the illustrated embodiment, the present invention is not limited to use of such claws 36 but claws of various planar shapes may be selectively used. With the claws 36 of any planar shape being used, the orientation of the fibrous nonwoven fabric in the longitudinal direction Y reliably reinforces the engagement of the claws with the fibrous nonwoven fabric.

Strengthened engagement between the hook elements and the target fibrous nonwoven fabric assured in this manner allows the target to be selected from various types of fibrous nonwoven fabrics without being limited to one or more specific types of fibrous nonwoven fabric.

For the present embodiment, usually used elastomeric member such as rubber string or rubber ribbon or elastically stretchable and contractible film may be used as the flaps' elastic members 24. In this regard, it should be noted here that, if single elastic film dimensioned to cover the entire area of the respective contractible region 23, the contractible region will disadvantageously thickened and may lead not only to deterioration of feeling to wear and air-permeability of the diaper but also to increased cost. Such problem is significant in the adult diaper of which each of the flaps 16 has a correspondingly larger area. Taking account of this, when the elastically contractible film is used as the flaps' elastic members 24, it is desired to use these elastic members 24 in the form of a plurality of elastic film ribbons spaced one from another. These elastic members 24 may be replaced by elastic nonwoven fabric. In this case also, such elastic nonwoven fabric is preferably used in the form of a plurality of elastic nonwoven fabric ribbons spaced one from another in consideration of feeling to wear and air-permeability. However, the elastic member made of rubber or the like is preferably used when greater emphasis is placed on durability and cost.

It is also possible to combine an elastic nonwoven fabric with an inelastic nonwoven fabric to form the contractible region 23. As the elastic nonwoven fabric, for example, a nonwoven fabric formed by commingling PP fiber and urethane fiber may be used. In this case, the inelastic nonwoven fabric may be bonded to the elastic nonwoven fabric under tension to obtain the contractible region 23.

The joint regions 19 lying inboard of the respective contractible regions 23 are not provided with the flaps' elastic members 24 to define non-contractible regions. The joint regions 19 made inelastic in this manner facilitate the diaper 1 to be put on the wearer's body. Specifically, for example, when the diaper is put on the wearer's body lying down on a bed, the diaper 1 is inserted between the wearer's buttocks and the bed and the first and second hook elements 21, 22 are put in engagement with the outer sheet 8 while the flaps 16 are pulled to adjust a positional relation with the wearer's buttocks. In the course of such handling, high tensile force is exerted on the flaps 16 and in the case of the flaps 16 provided with the elastic members attached thereto to extend fully across the respective flaps 16, it will be impossible to adjust the positional relation with the wearer's buttocks merely by pulling the flaps 16. In the case of such flaps 16, there is another possibility that the flaps 16 might be excessively pulled to adjust the positional relation and eventually the flaps 16 might be torn. According to the present embodiment, such problems are solved by formation of the non-contractible regions. It is possible to adjust the positional relation by directly holding these non-contractible regions to pull the flaps 16.

Each of the joint regions 19 is formed of total four sheets, i.e., the flap sheets 17, 18 forming the flap 16 and inner and outer sheets 7, 8 forming the rear waist region 5 and the joint region 19 would not be torn even when this joint region 19 is gripped and pulled. While the flap 16 is prepared separately of the chassis 2 and attached to the latter according to the present embodiment, it is possible to form the chassis 2 directly with the first and second hook elements 21, 22 and the contractible regions 23.

The flaps' elastic members 24 are provided outboard of the leg-surrounding elastic members 25 as viewed in the transverse direction X so that the flaps' elastic members 25 may lie between opposite ends of the leg-surrounding elastic members 25 curving in U-shape as the diaper 1 is put on the wearer's body. By locating the flaps' elastic members 24 in this manner, the flaps' elastic members 24 apparently become contiguous to the leg-surrounding elastic members 25 and annular peripheral edges surrounding the respective legs. The leg-openings' peripheral edges of the diaper 1 are noticeably stretched, for example, as the wearer having the diaper 1 put on his or her body crouches down but the tensile force of these peripheral edges is evenly distributed along these peripheral edges because the elastic members 24, 25 cooperate together to surround the wearer's legs. Furthermore, the elongation quantity of the leg-openings' peripheral edges may be increased by forming the leg-openings' peripheral edges by the leg-surrounding elastic members 25 plus the flaps' elastic members 24. In this way, the entire peripheral edges of the respective leg-openings can smoothly follow movement of the wearer.

Figure 5:
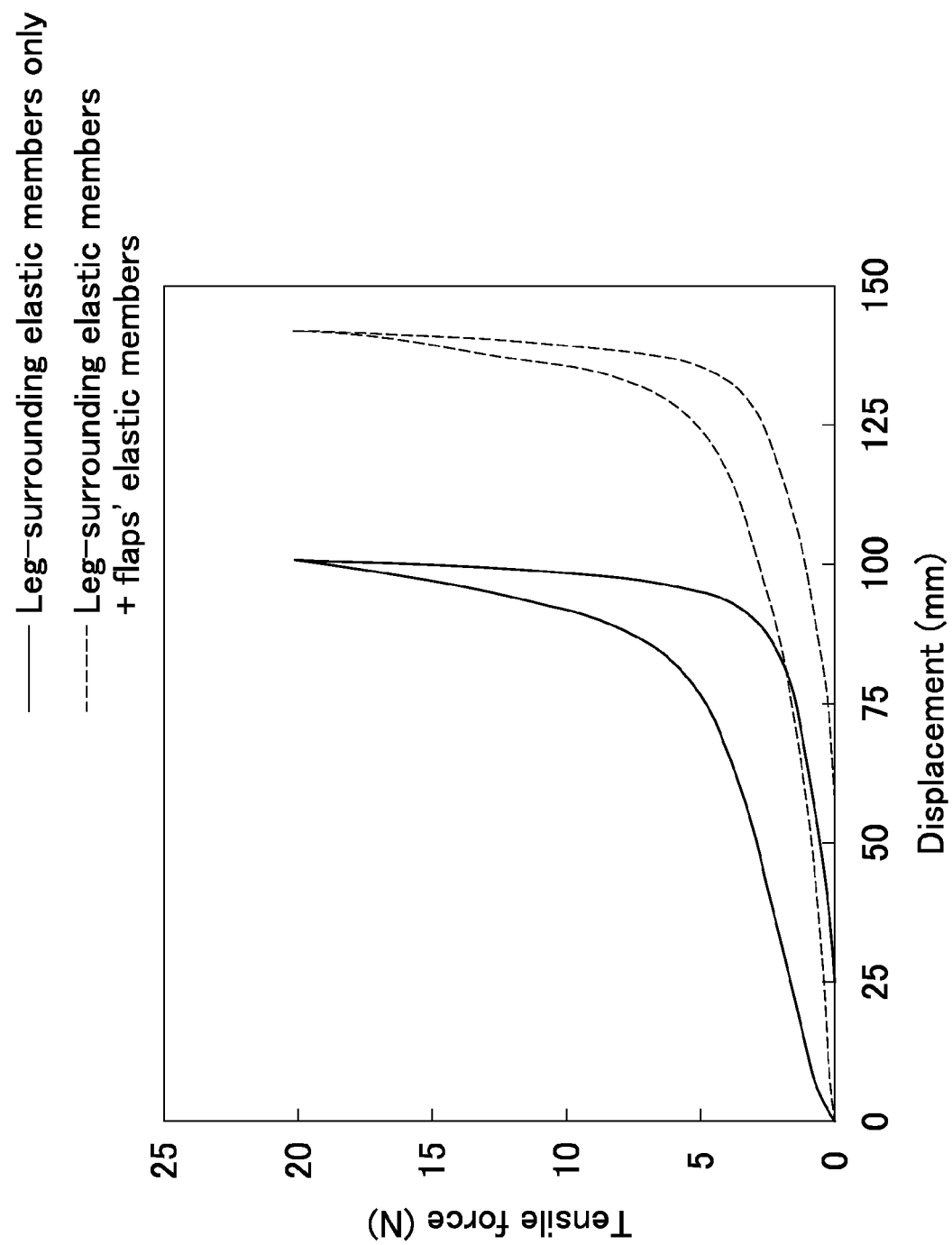
FIG. 5 is a graphic diagram plotting displacement of the leg-openings peripheral edges versus tensile force exerted thereon.

FIG. 5 is a graphic diagram comparatively plotting the relation of displacement versus tensile force with respect to the case in which the leg-openings' peripheral edges are defined only by the leg-surrounding elastic members and to the case in which the leg-openings' peripheral edges are defined by the leg-surrounding elastic members and the flaps' elastic members. Specifically, in the state wherein the diaper is put on the wearer's body, i.e., the first and second hook elements are put in engagement with the target nonwoven fabric, a pair of metering rods are inserted into the leg-opening, then one of these rods is fixed and the other rod is moved away from the fixed rod to measure the tensile force (N) exerted on this metering rod and the displacement (mm) of the leg-opening's peripheral edge. Values measured with respect to the case in which the peripheral edge is defined only by the leg-surrounding elastic members is indicated by solid lines and value measure with respect to the case in which the peripheral edge is defined by the leg-surrounding elastic members plus the flap's elastic members is indicated by dashed lines. Both the solid line and the dashed line are paired in this graphic diagram wherein the lines on the left side plot the values measured as the tensile force is gradually turned up by moving the metering rod is gradually spaced from the fixed metering rod and the lines on the right side plot the values measured as the tensile force is gradually reduced by turning back the metering rod which has been once spaced from the fixed metering rod.

As will be apparent from FIG. 5, while there is no substantial difference of the displacement after the tensile force had exceeded 5 N, the displacement under the tensile force of 5 N was about 75 mm in the case wherein the leg-opening's peripheral edge is defined only by the leg-surrounding elastic members and about 125 mm (i.e., about 1.7 times higher than the former case) in the case wherein the leg-opening's peripheral edge is defined by the leg-surrounding elastic members+ the flap's elastic members.

As has been described just above, it is possible to prevent the tensile force from being concentrated on the flap 16 and thereby to restrict the possibility that an excessive tensile force tending to shear the engagement between the first and second hook elements 21, 22 and the outer sheet 8 might be generated. In this way, in the course of putting the diaper on the wearer's body, the first and second hook elements 21, 22 and the outer sheet 8 having been once engaged together would not be disengaged so that the front and rear waist regions 4, 5 would not be disconnected from each other. While the relative position of the leg-surrounding elastic members 25 and the flap's elastic members 24 may be more or less variable depending on the individual wearer's physical size or the other factors, the leg-opening's peripheral edge is almost always defined by the elastic members 24, 25. It is not essential that the leg-opening's peripheral edge is defined by the leg-surrounding elastic members 25 and the flap's elastic members 24 in a complete annular shape and these elastic members 24, 25 may be more or less spaced one from another or overlap one another.

While the leg-surrounding elastic members 25 are rectilinearly arranged according to the present embodiment, it is possible to arrange these elastic members 25 to follow the curves of the crotch region's side edges. With such arrangement of the elastic members 25, it will be assured that the diaper more reliably fits around the wearer's thighs and the leg-surrounding elastic members 25 reliably cooperate with the flats' elastic members 24 to define the annular peripheral edges of the leg-openings. In consequence, the tensile force of the leg-openings' peripheral edges can be distributed as evenly as possible. It is also possible to curve the segments of the leg-surrounding elastic members 25 lying on the side of the front waist region's side edges 13 and to straighten the segments thereof lying on the side of the rear waist region's side edges 14. In this case, the segments of the leg-surrounding elastic members 25 lying on the side of the rear waist region's side edges cooperate with the joint regions 19 to define non-contractible regions.

According to the present embodiment also, it is unnecessary to employ any kind of loop elements as the target for the first and second hook elements 21, 22. This means that the target region can be kept soft without affecting the feeling to wear the diaper. By using a fibrous nonwoven fabric as the target, sound generated at the moment of peeling the hook elements off from the target can be minimized.

The outer sheet 8 is formed of the fibrous nonwoven fabric serving as the target and therefore it is unnecessary to employ any kind of loop elements. In this way, manufacturing cost can be correspondingly reduced. The entire outer sheet 8 can serve as the target and no particular engagement positions are specified. In other words, the hook elements can be appropriately put in engagement with the outer sheet 8 depending on the individual wearer's physical size or the other factors. Furthermore, the engagement of the hook elements with the target fibrous nonwoven fabric can be fortified by orienting the component fibers thereof and various types of nonwoven fabric can be used as the target without being limited to any particular type of nonwoven fabric.

Second Embodiment

Figure 6:
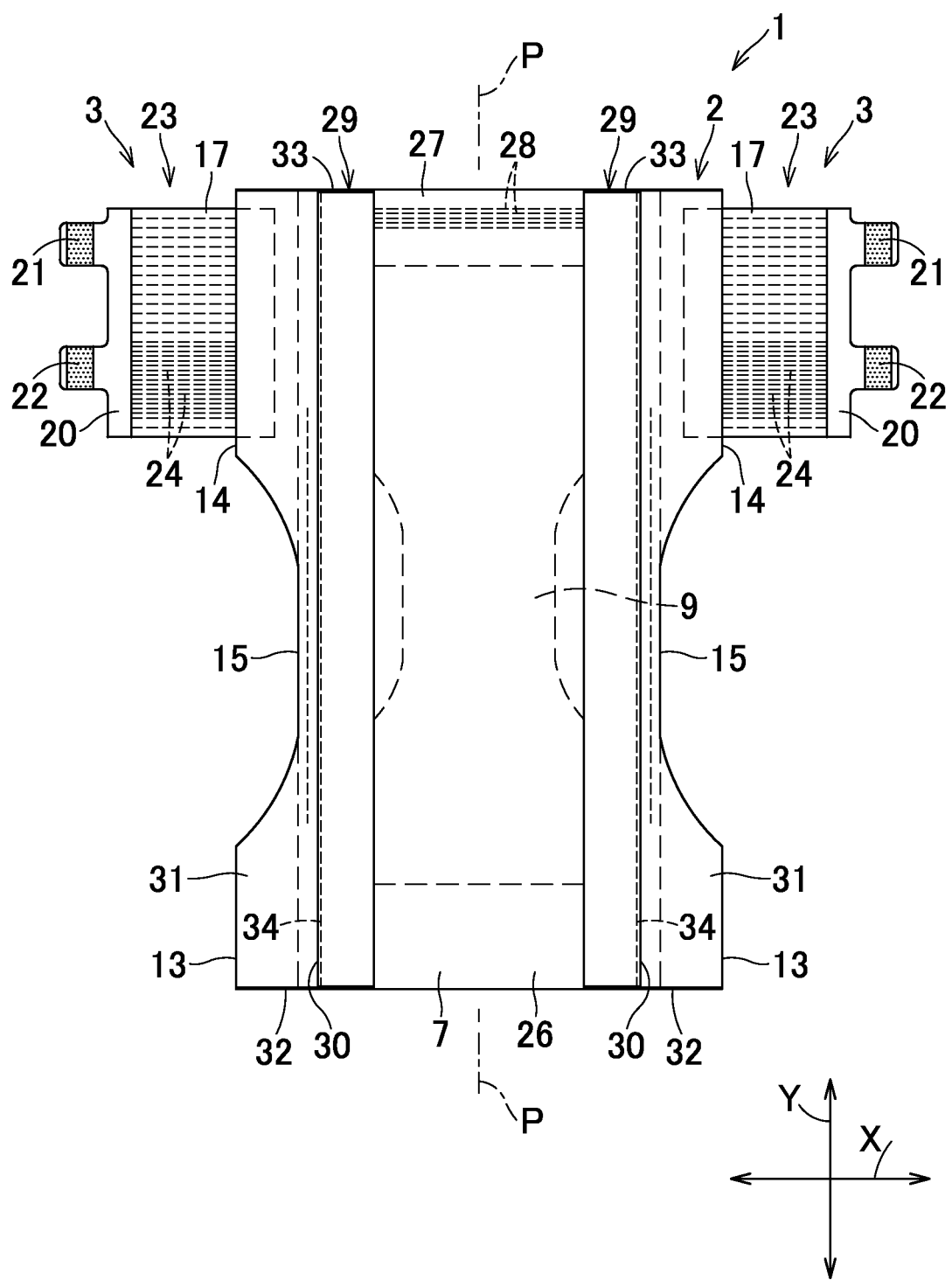
FIG. 6 is a plan view showing the diaper according to a second embodiment of the present invention as kept in flatly developed.

FIG. 6 shows a second embodiment of the present invention.

One of the features in the second embodiment is leak-barrier cuffs 29 provided on the skin-facing side of the inner sheet 7. Another feature is locations at which the flaps' elastic members 24 are attached to the diaper. The features other than these two features are similar to those in the first embodiment and these similar features will not be repetitively described.

The leak-barrier cuffs 29 extending between the front and rear ends 26, 27 of the chassis 2 in the longitudinal direction Y, shaped symmetrically about the longitudinal center line P-P and opposed to each other in the transverse direction X. Each of the leak-barrier cuffs 29 has inner and outer side edges 30, 31 opposed to each other in the transverse direction X and extending in the longitudinal direction Y and front and rear ends 32, 33 opposed to each other in the longitudinal direction Y and extending in the transverse direction X. The outer side edge 31 is bonded to the inner sheet 7 to define a fixed side edge and the inner side edge is left not bonded to the inner sheet 7 to define a free edge. The inner side edge 30 is folded outward as viewed in the transverse direction X and bonded at the front and rear ends 32, 33 to the inner sheet 7. The inner side edge 30 is provided with cuff's elastic member 34 bonded under tension to extend in the longitudinal direction Y. Upon contraction of the cuff's elastic member 34, the free edge is spaced upward from the inner sheet 7 and thereby functions to prevent leak of body waste such as urine.

According to the present embodiment, the interval at which a plurality of the flap's elastic members 24 may be arranged are variable in the longitudinal direction Y. Specifically, the flap's elastic members 24 are arranged at a relatively narrow interval in a lower section of the flap 16 as viewed in FIG. 6 and at a relatively wide interval in an upper section of the flap 16. The flap's elastic members 24 arranged at the relatively narrow interval in the lower section of the flap 16 operates so that, even when the flap 16 is pulled with even force, the diaper 1 fits to the wearer's body with relatively high tightness in the lower section of the flap 16, i.e., in the vicinity of the leg-opening's peripheral edge. In contrast, the diaper 1 fits to the wearer's body with relatively low tightness in the upper section of the flap 16, i.e., on the side of the waist regions. For example, for the wearer lying down on his or her bed for much time in everyday, tightness may be adjusted to be relatively high in the vicinity of the leg-opening's peripheral edge as the present embodiment in order to give greater importance to prevention of leakage.

While the flap's elastic members 24 are arranged at a relatively narrow interval in the lower section of the flap 16 in FIG. 6, it is possible to set the interval relatively narrow in the upper section of the flap 16. Such arrangement is suitable for the wearer who can freely move his or her body, for example, freely stand up and sit down. This is for the reason that, for such wearer, a premium is placed on prevention of displacement of the diaper 1 rather than prevention of leakage and, for this purpose, tightness is often set to be relatively high on the side of the waist regions.

The tensile stress of the flap 16 in its contractible region 23 may be adjustably varied depending on the individual wearer to achieve comfortable feeling to wear the diaper 1 for the individual wearer.

It is possible to make the tensile stress of the contractible region differential by differentiating the elongation percentage of the flap's elastic members 23 in the longitudinal direction Y. Specifically, the elongation percentage of certain of the elastic members 23 may be set to be higher than the elongation percentage of the remaining elastic members 23 to make the tensile stress of the former higher than the tensile stress of the latter and vice versa. It is also possible to make the tensile stress of the contractible region differential by differentiating the elastic members' diameters. Specifically, the diameter of certain of the elastic members 23 is set to be larger than the diameter of the remaining elastic members 23 to make the tensile stress of the former higher than the tensile stress of the latter and vice versa.

Figure 7A:
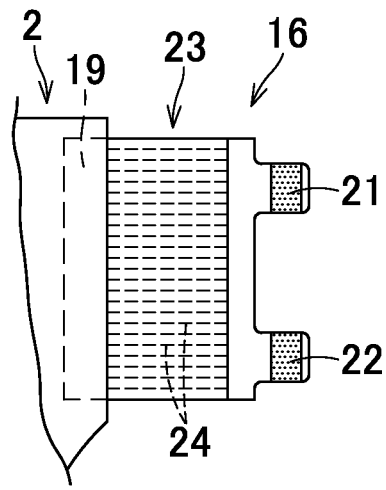
FIG. 7 is a diagram illustrating preferred embodiments of a flap according to the present invention.
Figure 7B:
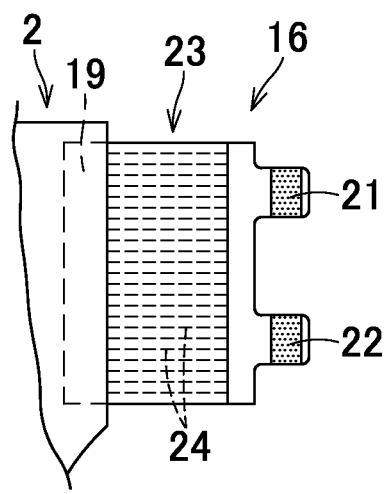
Figure 7C:
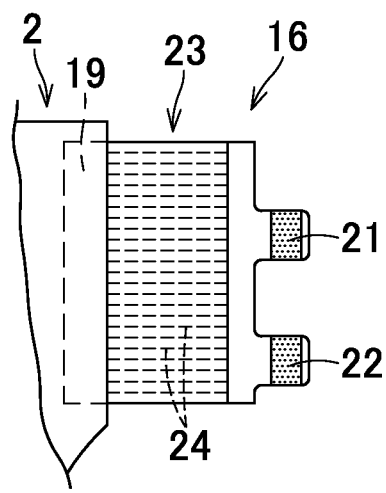

As further alternative method to make the tensile stress of the stretchable region 23 variable, it is also possible to position the first and second hook elements 21, 22 in various manners as exemplarily illustrated by FIG. 7. As illustrated by FIG. 7A, the first and second hook elements 21, 22 may be positioned substantially at a same distance from upper and lower ends of the flap 16, respectively, to distribute the tensile stress almost evenly in the longitudinal direction Y. Compared to the positioning as illustrated by FIG. 7B, the second hook elements 22 may be positioned upward as viewed in the longitudinal direction Y of the flap 16, i.e., closer to the first hook elements 21 as illustrated by FIG. 7B to make the tensile stress relatively high in the lower section of the flap 16. Finally, the first hook elements 21 may be positioned downward as viewed in the longitudinal direction Y of the flap 16, i.e., closer to the second hook elements 22 as illustrated by FIG. 7C to make the tensile stress relatively high in the upper section of the flap 16.

According to the present embodiment, the tensile stress of the contractible regions 23 can be changed and appropriately adjusted depending on the wearer's personal factors such as physical size and life style so that individual users may feel comfortable to wear.

The invention claimed is:

1. A wearing article comprising:
   a chassis having:
      a longitudinal direction and a transverse direction;
      a skin-facing side and a garment-facing side;
      a front waist region;
      a rear waist region;
      a crotch region extending between these front and rear waist regions; and
   fastening means serving to connect respective opposite side edges of said front and rear waist regions in a detachable manner and thereby to connect said front and rear waist regions to each other in a circumferential direction,
   said fastening means comprising:
      hook elements provided on one of said front and rear waist regions and a target fibrous nonwoven fabric provided on other of said front and rear waist regions and adapted to be detachably engaged with said hook elements; and
      contractible regions adapted to be contractible in the transverse direction are provided inboard of said hook elements as viewed in said transverse direction
      wherein said hook elements each comprise a first hook element and a second hook element, said first hook elements and said second hook elements being spaced apart from each other in the longitudinal direction, with said second hook elements being position below said first hook elements in the longitudinal direction and said second hook elements and said first hook elements having the same width in the longitudinal direction, and
      the distance from an upper end of said contractible region to an upper end of said first hook element is different from a distance from a lower end of said contractible region to a lower end of said second hook element as measured in the longitudinal direction.

2. The wearing article defined by claim 1 wherein:
   said chassis further comprises an inner sheet defining said skin-facing side and an outer sheet defining said garment-facing side; and said outer sheet is formed of said target fibrous nonwoven fabric.

3. The wearing article defined by claim 2, wherein non-contractible regions having no elasticity are formed contiguously to respective said contractible regions.

4. The wearing article defined by claim 3, wherein said target fibrous nonwoven fabric comprising component fibers oriented in said longitudinal direction.

5. The wearing article defined by claim 4, wherein said contractible regions include a plurality of elastic members or elastic nonwoven fabric ribbons, said elastic members or said elastic nonwoven fabric ribbons are attached under tension to said contractible regions to be spaced one from another in the longitudinal direction and to extend in said transverse direction.

6. The wearing article defined by claim 3, wherein said contractible regions include a plurality of elastic members or elastic nonwoven fabric ribbons, said elastic members or said elastic nonwoven fabric ribbons are attached under tension to said contractible regions to be spaced one from another in the longitudinal direction and to extend in said transverse direction.

7. The wearing article defined by claim 2, wherein said target fibrous nonwoven fabric comprising component fibers oriented in said longitudinal direction.

8. The wearing article defined by claim 7, wherein said contractible regions include a plurality of elastic members or elastic nonwoven fabric ribbons, said elastic members or said elastic nonwoven fabric ribbons are attached under tension to said contractible regions to be spaced one from another in the longitudinal direction and to extend in said transverse direction.

9. The wearing article defined by claim 2, wherein said contractible regions include a plurality of elastic members or elastic nonwoven fabric ribbons, said elastic members or said elastic nonwoven fabric ribbons are attached under tension to said contractible regions to be spaced one from another in the longitudinal direction and to extend in said transverse direction.

10. The wearing article defined by claim 1, wherein non-contractible regions having no elasticity are formed contiguously to respective said contractible regions.

11. The wearing article defined by claim 10, wherein said target fibrous nonwoven fabric comprising component fibers oriented in said longitudinal direction.

12. The wearing article defined by claim 11, wherein said contractible regions include a plurality of elastic members or elastic nonwoven fabric ribbons, said elastic members or said elastic nonwoven fabric ribbons are attached under tension to said contractible regions to be spaced one from another in the longitudinal direction and to extend in said transverse direction.

13. The wearing article defined by claim 10, wherein said contractible regions include a plurality of elastic members or elastic nonwoven fabric ribbons, said elastic members or said elastic nonwoven fabric ribbons are attached under tension to said contractible regions to be spaced one from another in the longitudinal direction and to extend in said transverse direction.

14. The wearing article defined by claim 1, wherein said target fibrous nonwoven fabric comprising component fibers oriented in said longitudinal direction.

15. The wearing article defined by claim 14, wherein said contractible regions include a plurality of elastic members or elastic nonwoven fabric ribbons, said elastic members or said elastic nonwoven fabric ribbons are attached under tension to said contractible regions to be spaced one from another in the longitudinal direction and to extend in said transverse direction.

16. The wearing article defined by claim 1, wherein said chassis further includes leg-surrounding elastic members attached under tension along said side edges to extend in said longitudinal direction and said contractible regions cooperate with said leg-surrounding members as the diaper is put on the wearer's body to form annular peripheral edges of the respective leg-openings.

17. The wearing article defined by claim 16, wherein said contractible regions include a plurality of elastic members or elastic nonwoven fabric ribbons, said elastic members or said elastic nonwoven fabric ribbons are attached under tension to said contractible regions to be spaced one from another in the longitudinal direction and to extend in said transverse direction.

18. The wearing article defined by claim 16, wherein said contractible regions are arranged to lie outboard of leg-surrounding elastic members as viewed in the transverse direction.

19. The wearing article defined by claim 1, wherein said contractible regions include a plurality of elastic members or elastic nonwoven fabric ribbons, said elastic members or said elastic nonwoven fabric ribbons are attached under tension to said contractible regions to be spaced one from another in the longitudinal direction and to extend in said transverse direction.

20. The wearing article defined by claim 1, further comprising reinforcing sheets that extend from the contractible regions in the transverse direction and are provided with the first and second hook elements.

21. The wearing article defined by claim 1, wherein said chassis has front and rear ends defined by said front and rear waist regions, respectively, which front and rear ends extend in the transverse direction; and the upper ends of said contractible regions provided on said front and rear waist regions are located below said front and rear ends as viewed in the longitudinal direction.

* * * * *

UNITED STATES PATENT AND TRADEMARK OFFICE
CERTIFICATE OF CORRECTION

PATENT NO. : 8,663,185 B2  
APPLICATION NO. : 12/865906  
DATED : March 4, 2014  
INVENTOR(S) : Katsumi Mizutani et al.

Page 1 of 1

It is certified that error appears in the above-identified patent and that said Letters Patent is hereby corrected as shown below:

In the Specification

Column 7, line 34, delete "□" and substitute --x-- in its place.

Column 7, line 36, delete "□" and substitute --x-- in its place.

Column 7, line 45, delete "□" and substitute a --°-- in its place.

Signed and Sealed this
Twenty-seventh Day of October, 2015

Michelle K. Lee
*Director of the United States Patent and Trademark Office*